United States Patent [19]

Landsness et al.

[11] Patent Number: 4,498,042
[45] Date of Patent: Feb. 5, 1985

[54] MAT TESTING APPARATUS

[75] Inventors: Clifford A. Landsness; Thomas M. Buehrle, both of Akron, Ohio

[73] Assignee: The B. F. Goodrich Company, New York, N.Y.

[21] Appl. No.: 441,146

[22] Filed: Nov. 15, 1982

[51] Int. Cl.³ .............................................. G01R 31/12
[52] U.S. Cl. .................................................... 324/54
[58] Field of Search ...................... 324/54, 51; 340/647

[56] References Cited

U.S. PATENT DOCUMENTS

4,247,814  1/1981  Landsness ............................ 324/54
4,347,477  8/1982  Landsness ............................ 324/54

Primary Examiner—Stanley T. Krawczewicz
Attorney, Agent, or Firm—Joseph Januszkiewicz

[57] ABSTRACT

A high voltage mat testing apparatus which tests successive spaced portions of the mat in a test chamber which houses replaceable test plates to accommodate different widths of matting material.

9 Claims, 6 Drawing Figures

MAT TESTING APPARATUS

BACKGROUND OF THE INVENTION

This invention relates to a new and improved apparatus for testing the non-conductance of rubber matting under the application of high voltage.

Where electrical repairs are made in areas that have good electrical conductive substances such as steel or metal, it is necessary to provide an insulating mat that is relatively thin and lightweight on which the repairman may stand to assure his safety from electrical shocks. Such mats or matting materials must be portable so that the mats can be rolled out for use in a prescribed area and thence re-rolled and moved to the next location. It is necessary that such matting withstand high voltages. Such matting is particularly useful in areas such as decks of ships where there are electrical control panels and switch gears to provide proper insulation of the power stations from electrical shorts as well as provide safety for the workers at their locations. Apparatus used to test the dielectrical properties of such matting had means for unrolling small sections thereof for testing as to its resistance to the application of a high voltage. After one section or a portion of the roll is tested, the roll of matting material is advanced such as to position a new section for testing. Such process is slow. A further recent method and apparatus used a pair of spaced rolls that intermittently tested two spaced predetermined lengths of the matting material as it was transferred from one roll to the second roll. These machines were limited to a specific type and width of material as well as to its thickness. The present invention provides means for automatically testing spaced portions of different widths of materials as well as different thicknesses by providing replaceable deck plates that accommodated different sizes of matting materials to provide a versatile means for testing the dielectric properties of the matting materials. This test procedure and apparatus permits the continuous testing of the dielectric properties of different width and thickness materials in an economical manner without requiring a new test machine for different sizes. In addition by using a resilient foam member to back the metal plate member, variations in thickness of test material are accommodated by the test apparatus.

SUMMARY OF THE INVENTION

The present invention contemplates an apparatus for applying a high voltage charge in seriatim order to successive spaced portions of an electrical non-conductive matting such as a rubber mat as it unwound from a supply roll to a take-up roll by feeding such material past replaceable test plates. Provisions are made to overlap the testing of the successive spaced strips or portions of the matting by such plates to assure a testing of the full length of the matting.

DETAILED DESCRIPTION

Figure 1:
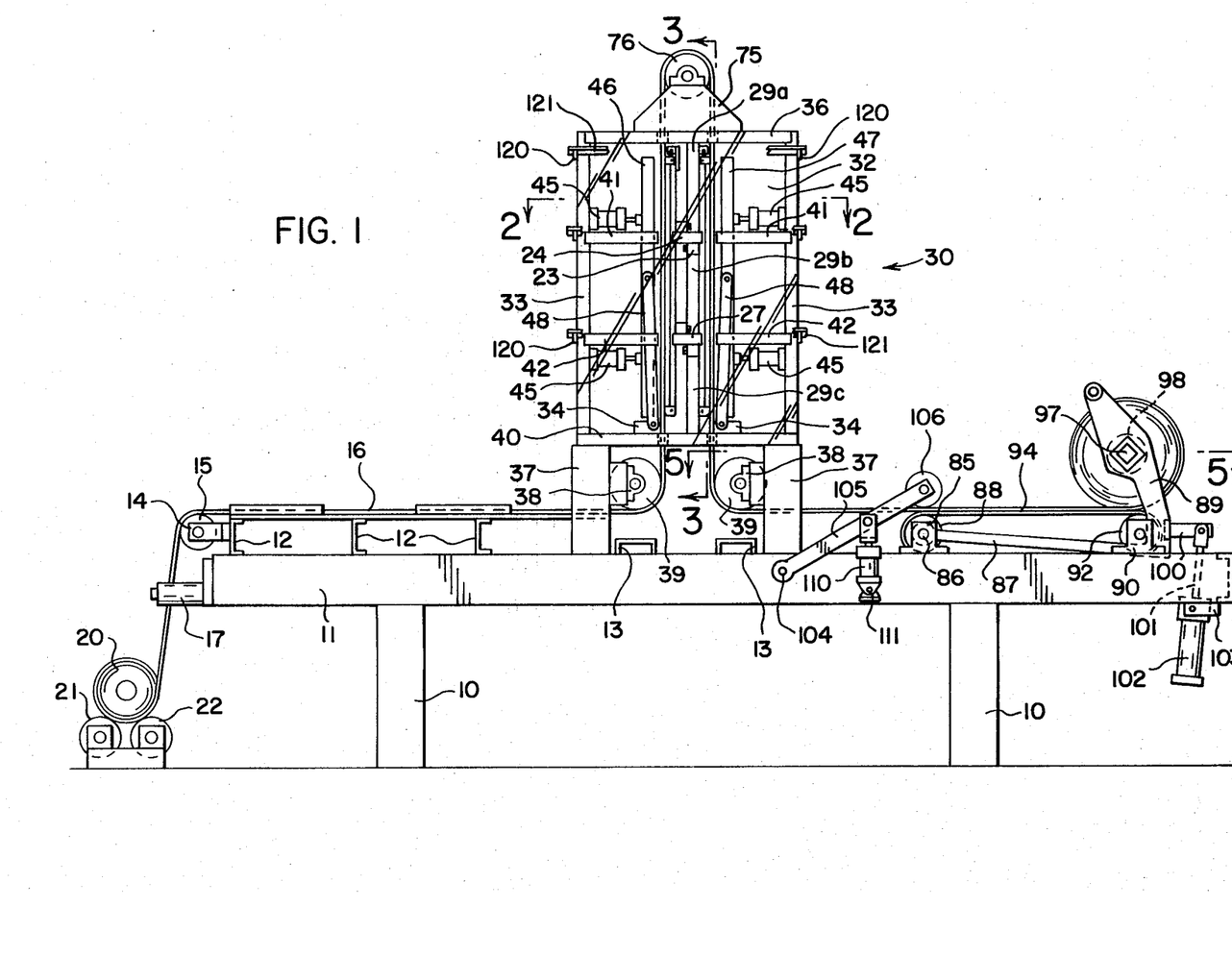
FIG. 1 is a side elevational view of a mat testing apparatus.

Referring to the drawings, wherein like reference numerals designate like or corresponding parts throughout the several views, there is shown in FIG. 1 a plurality of vertical supports 10 supporting brackets 11 which in turn support cross braces 12 and channel beams 13. Mounted on one of the cross braces 12 is a pair of spaced brackets 14 journaling for rotation a guide roller 15 over which matting 16 is guided. Side guide rollers 17—17 cooperate with the guide roller 15 to guide the matting as it passes from the supply roll 20 to the high voltage housing and its test chamber to be described. Supply roll 20 is supported by a pair of spaced idler rollers 21-22 to facilitate the unwinding of the matting material as it is advanced in a manner to be described.

Figure 2:
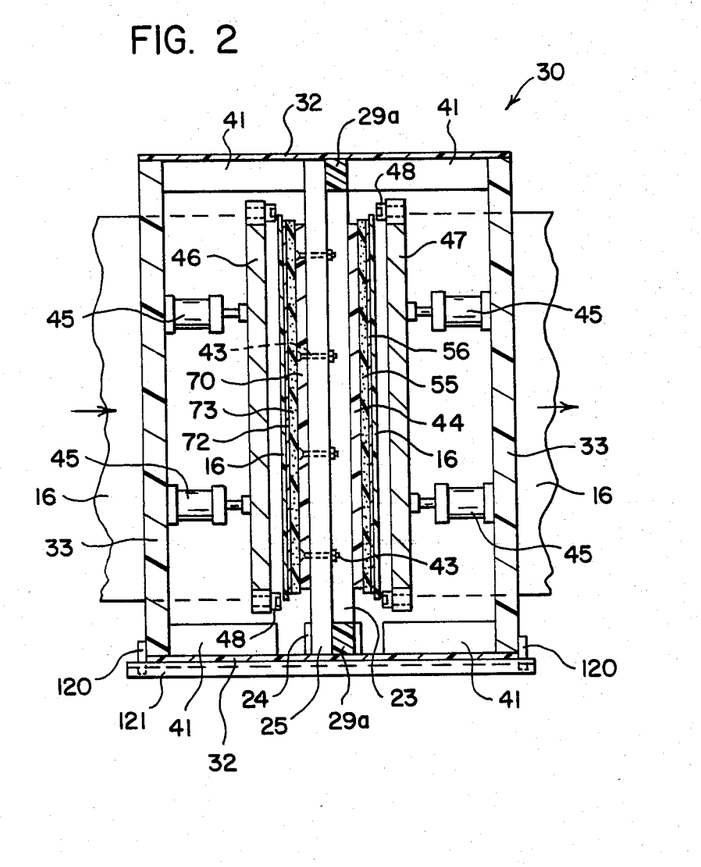
FIG. 2 is a cross-sectional view of the testing chamber taken on line 2—2 of FIG. 1.
Figure 3:
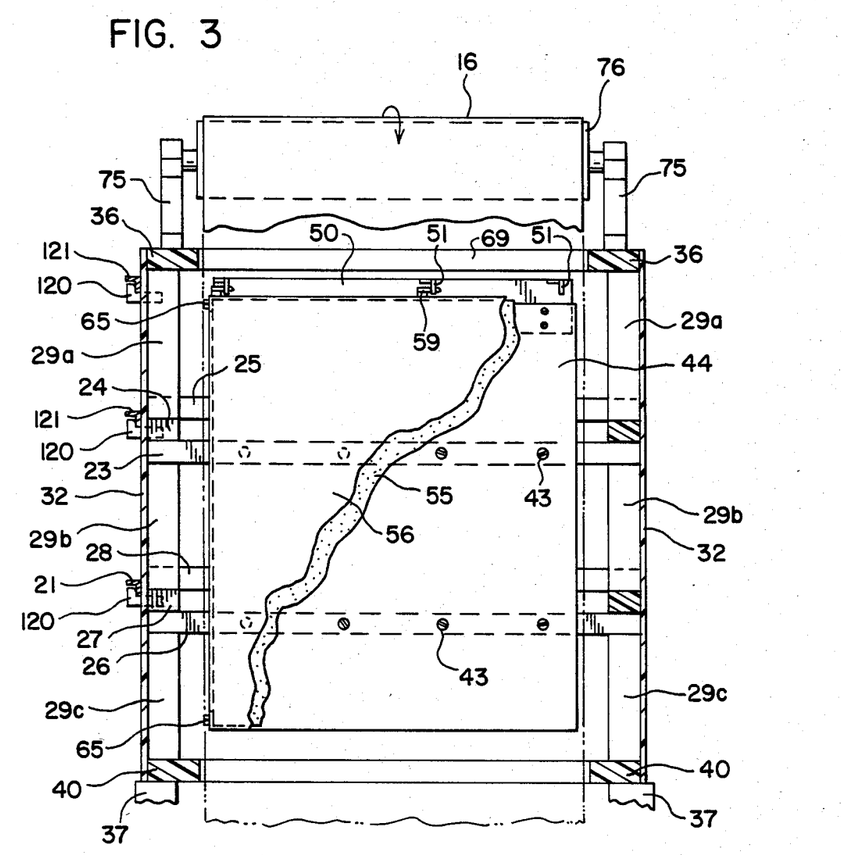
FIG. 3 is a front elevational view of the high-voltage testing chamber.
Figure 4:
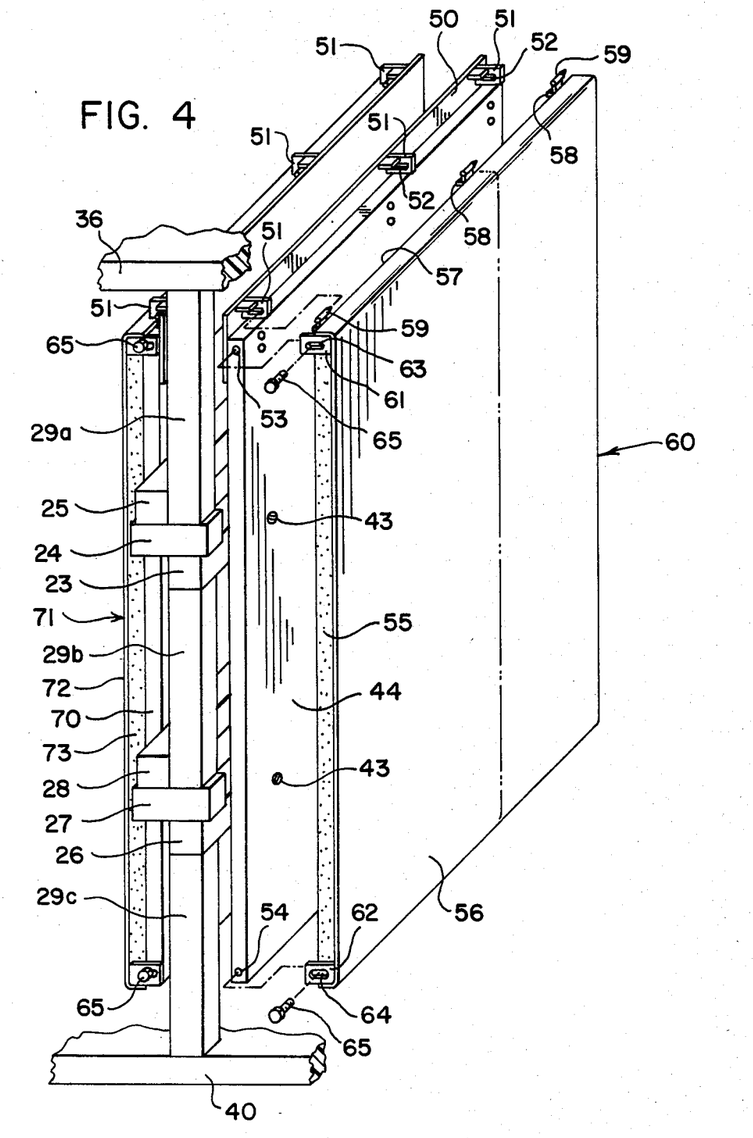
FIG. 4 is a perspective view of the interchangeable electrical conductive plates and their supports.
Figure 5:
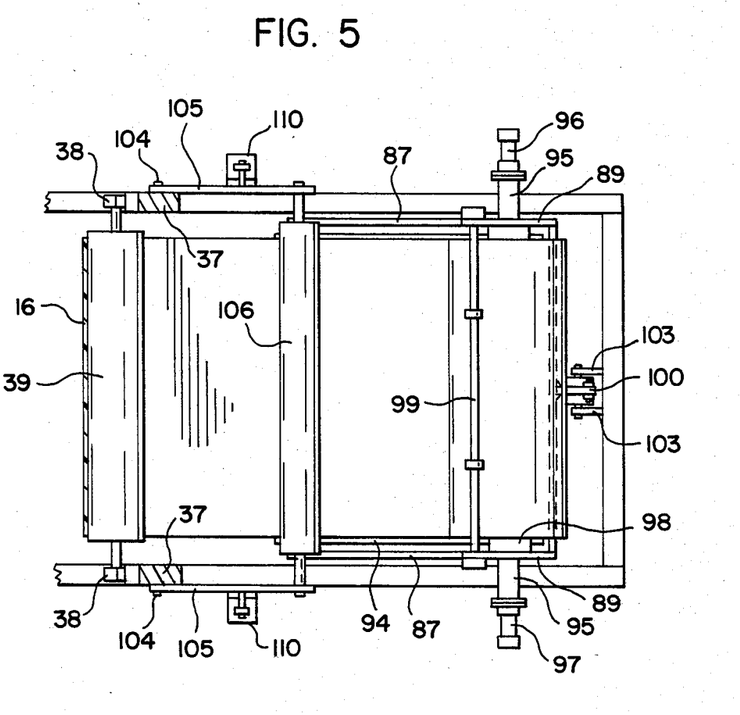
FIG. 5 is a plan view taken on lines 5—5 of FIG. 1 of a portion of the mat testing apparatus disclosing the take-up roller and adjacent conveying apparatus.

Suitably mounted over channel beams 13 is a housing test chamber 30 which includes vertical frame members 29a-29b-29c and spaced side members 33 (FIG. 2) supporting transparent side windows 32 such as clear polycarbonate. The vertical frame members located on the intermediate portion of the respective sides of the test chamber housing 30 as seen in FIGS. 3 and 4 consists of three sections vertically aligned 29a, 29b and 29c. Sections 29a and 29b are separated by a cross brace 23 (FIGS. 1 and 4) and rectangular shaped blocks 24 mounted on both ends of brace 23. A cross brace 25 spans the respective blocks 24 and is suitably connected thereto. The respective blocks 24 and cross brace 25 are connected to the vertically disposed section 29a. In a similar manner sections 29b and 29c are separated by a cross brace 26 and rectangular shaped blocks 27 mounted on both ends of brace 26. Cross brace 26 spans the respective blocks 27 and is suitably connected to such blocks 27 and vertical frame member 29c. The blocks 27 and cross brace 28 are connected to the vertically disposed section 29b. The upper ends of windows 32 are abutted by a pair of upper bracket members 36. Members 29a, 29b, 29c, 33 and 36 cooperate with windows 32 to define the high voltage housing test chamber 30. Test chamber 30 is supported by spaced brackets 40 which in turn are mounted on vertical support braces 37. Pairs of journal housings 38 are mounted on braces 37 which support transfer rollers 39 therebetween. On the back side of housing 30, the cross braces extend along the entire back side, whereas on the front side (as seen in FIG. 1) the cross braces have gaps to permit the changing of the test plates as to be described. As shown in FIGS. 1, 3 and 4, bracket 40 extends along the full length at the bottom while plate member 36 extends along the full length of the top side. Also located on the front side of the housing 30 is a pair of spaced brackets 41 in line with block 24 and a pair of spaced brackets 42 in line with block 27. This construction provides a pair of gaps for the removal and insertion of new test plates. The cross braces 41 and 42 on the front side as seen in FIG. 1 can be supported by additional vertical braces, however, for clarity sake these braces are omitted and braces 41 and 42 are shown as contilever supported.

Suitably mounted on the oppositely disposed side members 33 are pneumatic cylinders 45. The rod end of the cylinders 45 are secured to a pair of spaced electrically conductive plates or electrode platens 46-47. A suitable electrical power source for supplying a high voltage is connected to vertically extending plates 46 and 47. Suitable limit switches are mounted on the braces 41 and 42 and are operative to be actuated by abutments on the piston rods of the cylinders 45 to facilitate the sensing and control of the platen's movement in a manner to be described.

The intermediate side of each plate or platen 46 and 47 is pivotally connected to one end of a lever arm 48 (FIG. 1). The other end of each lever arm 48 is suitably pivotally connected to lower cross braces 40 via support members 34. With the pressurization of the head end of the cylinders 45, the respective plates 46 and 47 are moved toward each other while pressurization of the rod end of each cylinders 45 moves the plates 46 and 47 away from each other, with lever arms 48 freely supporting such plates to facilitate such movements.

Rigidly secured to the cross braces 23 and 26 (FIGS. 1 and 4) via plastic bolts 43 is a rigid sheet member 44 made of plastic or polyvinyl chloride. The upper end of sheet member 44 has a longitudinally extending plate member 50 suitably attached thereto. A plurality of laterally spaced brackets 51 are secured to the plate member 50. Each bracket 51 has an elongated slot 52. The respective one side edge of the rigid plastic sheet member 44 has threaded bores 53 and 54 adjacent the respective upper and lower ends thereof.

A flat planar sheet of deformable foam material 55 has a flat thin sheet of metal 56 such as stainless steel suitably adhered to one side thereof. The metal sheet 56 curves over the respective upper and lower ends of the foam sheet 55 presenting an upper edge 57 that has a plurality of spaced brackets 58 welded or suitably secured thereto. Each bracket 58 has an elongated pin 59 suitably secured to the uppermost edge thereof along a portion of such pin 59. The free end of pin 59 is adapted to slide into bores 52 on brackets 51 to suspend metal sheet 56 and the foam sheet 55 as a unit, which unit comprises a stationary electrically conductive plate or electrode platen 60. To retain the electrode plate 60 in position within the test chamber 30, the respective upper and lower side edges of the metal sheet 56 has brackets 61 and 62 suitably welded thereto. Each of these brackets 61 and 62 have elongated bores 63 and 64 respectively which are in alignment with bores 53 and 54 respectively. Threaded bolts 65 extending through bores 63 and 64 and into threaded bores 53 and 54 interconnect the electrode plate 60 to the stationary support or rigid plastic sheet member 44.

A rigid sheet member 70 (FIG. 4) similar to member 44 made of plastic or polyvinyl chloride is rigidly secured to the cross bars 25 and 28 via plastic bolts. An electrode plate 71 substantially identical to the electrode plate 60 is removably secured to the sheet member 70 in the same manner as plate 60 is secured to sheet member 44. Plate 71 has a electrically conductive metal sheet 72 and a foam sheet 73.

Upper bracket members 36 supports a pair of spaced brackets 75 (FIG. 3) which journal between them a roller 76 which operates to redirect dielectric material being tested from plates 46 and 71 to plates 47 and 60. Bracket members 36 support a plate member 69 which has suitable apertures to facilitate the movement of the dielectric material therethrough.

Suitably mounted on brackets 11 adjacent to the discharge end of high voltage testing chamber 30 are a pair of journals 85 which receive a shaft 86 journaling for rotation roller 88. Also mounted on brackets 11 at the rearwardmost end portion of the support frame are a pair of journals 90 supporting idler roller 92. Trained about rollers 88 and 92 is an endless belt 94 to facilitate the movement of the matting for windup in a manner to be described.

Suitably mounted on the bottom framework of the apparatus described is a motor not shown that drives roller 88. Such motor that drives roller 88 is energized by suitable control means old and well known in the arts to advance the matting material in a manner to be described.

Journaled on shaft 86 for pivotal movement are a pair of L-shaped spaced lever arm members 87 whose leg portions 89 support a housing member 95 on which is mounted pneumatic cylinders 96 and 97. Cylinders 96 and 97 are operative to actuate chuck means to release or mount a wind-up roller 98 that provide the support for the winding up of the matting thereabout. The respective ends of leg portions 89 are interconnected by a rod 99. The rear of leg portions 89 adjacent to lever arm members 87 are connected to a bracket 100, which bracket 100 is connected to a piston rod 101 of a pneumatic cylinder 102. Cylinder 102 is pivotally connected to braces 103 such that energization of the head end of cylinder 102 pivots lever arm members 87 counterclockwise about shaft 86 as seen in FIG. 1, which lifts the matting roller or roll 98 (FIG. 1) upwardly out of contact with the belt 94 and roller 92; whereas exhausing of the head end of cylinder 102 allows the matting being wound about roller 98 to rest on the belt 94, which belt 94 is in contact with the roller 92. The windup of the matting onto roller 98 would automatically compensate for its increase in diameter to provide a constant peripheral speed.

Pivotally mounted as at 104 on the spaced brackets 11 adjacent to one cross channel beam 13 is a pair of spaced lever arm members 105 which support for rotation a roller 106. A pair of spaced pneumatic cylinder 110 have their respective head ends pivotally secured as at 111 to supporting brackets 11. The respective piston rods of cylinders 110 are pivotally connected to the intermediate portion of lever arm members 105 for raising and lowering lever arm members 105 and idler roller 106 supported therebetween.

A plurality of vertically spaced Lshaped members 120 (FIGS. 1 and 3) are secured to the vertically disposed and horizontally spaced frame members 33. Upon placing of the front transparent window 32 in position, such that its lower edge rests on the brace 37, the window 32 can be locked in position by placing a horizontally extending locking bar 121 between horizontally spaced and aligned L-shaped members 120 such that the bar 121 has a portion thereof that snugly fits the space between the L-shaped member 120 and the window 32. Bar 121 can be a rectangular shaped member or L-shaped to facilitate the reception into the gap between the member 120 and the window 32 (FIG. 3).

Figure 6:
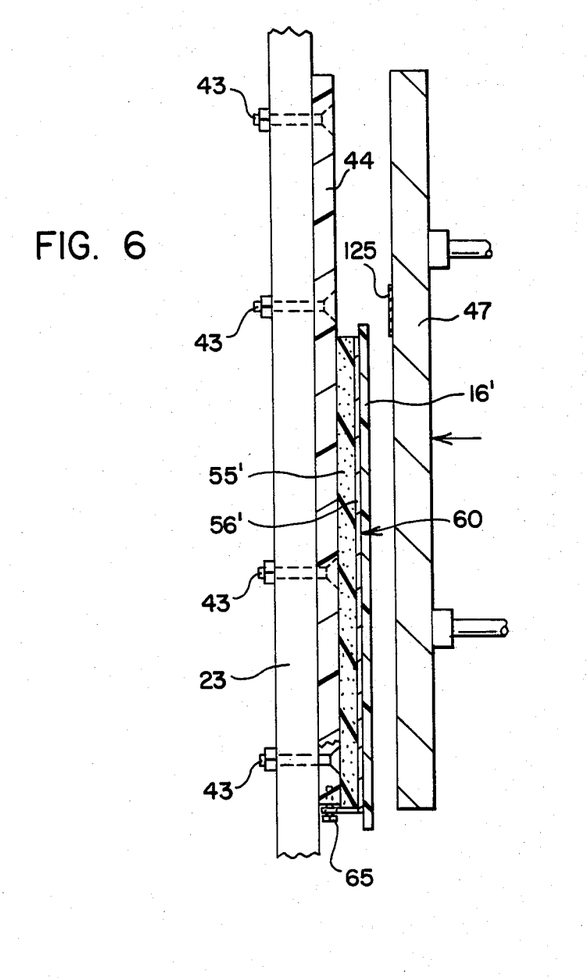
FIG. 6 is a plan view of a modified form of an interchangeable conductive plate.

In the operation of the mat tester, a roll of matting on a roller is placed between rollers 21 and 22 with the leader therefrom extending over roller 15 and fed into the test chamber 30, under forwardly disposed roller 39 and between plates 46 and 71, over roller 76, thence between plates 47 and 60, under rearwardly disposed roller 39 and thence between rollers 106 and 88 for attachment to the roller 98 which is supported by the leg portions 89 of arm members 87. The apparatus is now in a condition to test the insulating factor of the mat material at two spaced locations. The head end of cylinders 45 are actuated to move the respective spaced plates 46 and 47 into contact with the mat material whose opposite sides are supported by platens 71 and 60. A voltage such as 15,000 volts A.C. is applied from a suitable source to the respective plates 46 and 47. If the mat material is defective, a current will flow through the material to one of the grounded platens 60 or 71 which condition will be observed on the ammeter connected to the respective platens 60 and 71. Where no current flow is indicated after the prescribed time lapse, the rod end of pneumatic cylinders 45 are actuated which moves the respective electrode plates 46 and 47 out of contact with the matting in the test chamber 30, permitting the advancement of the matting such that new sections of matting are brought into position for testing by plates 46 and 47 with a slight overlap of the sections already tested to assure that the entire length of matting will be tested. This is accomplished by adjusting the rotation imparted by the motor for roller 88. Rotation of such motor rotates the endless belt 94 the prescribed distance. The mat material resting between rollers 88 and 106 will be advanced and the matting will be wound up onto roller 98 since roller 98 is frictionally resting on the belt 94. The mat material is advanced such that the portion of the mat material on roller 76 which is between plates 46 and 47 is advanced to be between plates 47 and 60 while the tested portion between platens 46 and 71 now overlies roller 76 and a new untested portion lies between platens 46 and 71. The operation will proceed until the entire roll of matting from roller 20 is expanded; however, a second roll of matting is placed onto the rollers 21 and 22 and spliced to the trailing end of the prior matting roll to facilitate uninterrupted passage through the test chamber 30.

Where a narrower width of matting material is to be tested after completion of a given run of wider width material, the replaceable platens 60 and 71 are removed from the test chamber 30. Changeover is begun by removal of the locking bar 121 and thence window 32. Thereafter bolts 65 are removed to permit the respective platens 60 and 71 to be removed laterally by separating the pins 59 from the slots 52 of brackets 51. As previously described the pins 59 permit the hanging of the respective platens 60 and 71 from the stationary plastic sheet members 70 and 44 and their corresponding brackets 51. The platens 60 and 71 are replaced by platens of suitable width, ones that are of substantially the same width as the mat material to be tested. As an example of a replaceable platen, note FIG. 6 discloses the regular size plastic sheet member 44 with the foam sheet 55' and the metal sheet 56' being of smaller width. In this case, the mat material 16' is slightly larger (in width) than the foam and metal sheets 55' and 56'. The moveable plate 47 is the same as used as in the first described embodiment. As the material is tested between the stationary metal sheet or plate 56' and the moveable electrode plate 47, it will be noted that an arcing can take place between the metal sheet 56' and the plate 47 in view of their close proximity at the edge of sheet 56'. Accordingly, a strip 125 of magnetized rubber is placed on the plate 47 such as to prevent any arcing between plate 47 and metal sheet 56'. In a similar manner the moveable plate on the other side of the housing is insulated electrically from its corresponding metal sheet and electrode plate. The rubberized strip 125 is placed in a vertically disposed attitude. Once the smaller width electrode plates are placed into position, the testing is performed in the same manner as described above. If desired the moveable plate 47 may be made removable by using the same structural features as disclosed by FIG. 4 utilizing either the rigid plastic member 44 and foam member 55 as well as thin sheet metal 56 or just plastic member 44 and sheet metal 56 along with the plate member 50, brackets 51 with slots 52 and pins 59 to provide ease of removal. In this manner arcing is prevented. The advantage of the first disclosed modification is that changeover is faster and thereby permits a more rapid testing of different sizes.

Other modifications are contemplated and may obviously be resorted to by those skilled in the art without departing from the described invention, as hereinafter defined by the appended claims, as only a preferred embodiment thereof has been disclosed.

We claim:

1. An apparatus for the testing of the electrical non-conductivity of an electrically non-conductive matting sheet material comprising support means having a forward portion and a rearward portion, a take-up roll maounted adjacent to said rearward portion of said support means for winding up said matting as said matting is directed thereto, at least a pair of flat electrode plates mounted on said support means intermediate of said forward and rear portions, power operated means mounted on said support means and interconnected to one of said pair of electrode plates for moving said one plate into a closely adjacent position to the other one of said plates to provide a small gap between said plates for testing electrical conductivity of said matting in said gap, means for applying a voltage to said one plate, gauge means connected to said other plate for registering a flow of voltage to said other plate from said one plate, means on said support means for feeding matting sheet material from a supply roll on said forward portion of said support means to between said electrode plates and for directing said matting material from between said electrode plates to said take-up roll, and at least one of said electrode plates being removably supported to provide the substituting of a different width electrode plate to facilitate the testing of different widths of matting sheet material between said electrode plates.

2. An apparatus for the testing of the electrical non-conductivity of matting sheet material as set forth in claim 1 wherein said one removable plate has a quick disconnect from said support means to facilitate replacement thereof.

3. An apparatus for the testing of the electrical non-conductivity of matting material as set forth in claim 2 wherein both of said plates are removably supported to permit quick replacement thereof.

4. An apparatus for the testing of the electrical non-conductivity of matting sheet material as set forth in claim 2 wherein said removable plate is a stationary plate and the remaining one of said plates is said moveable plate.

5. An apparatus for the testing of the electrical non-conductivity of matting sheet material as set forth in claim 4 wherein said stationary plate has an electrical non-conductive moveable insulating strip on the surface thereof to prevent short circuiting from said moveable plate wherein said plates are of different widths.

6. An apparatus for the testing of the electrical non-conductivity of matting sheet material as set forth in claim 5 wherein said stationary plate member is composed of a rigid dielectric backing member with a resilient plastic foam member abutting said rigid member, and a thin sheet of an electrical conductive member mounted on said resilient member on the surface opposite to said rigid backing member.

7. An apparatus for the testing of the electrical non-conductivity of matting sheet material as set forth in claim 6 wherein said rigid member is secured to said support means, said rigid member has a plurality of laterally spaced brackets mounted on the upper end thereof, said resilient member and said thin sheet of electrical conductive member define said removeable electrode plate, and said removeable plate has a plurality of laterally spaced pins along the upper end thereof for engagement with said brackets on said rigid member for mounting said removeable plate on said rigid member.

8. An apparatus for the testing of the electrical non-conductivity of a rubberized mat comprising support means having a forward portion and a rearward portion, at least two pairs of spaced flat electrode plates mounted on said support means intermediate of said forward and rearward portion, said plates are vertically disposed, power operated means mounted on said support means and interconnected to one of said plates in each of said pairs of electrode plates for moving said one plates respectively from a vertical storage position into a position closely adjacent to one of a remaining plates in each pair of plates to provide a small gap therebetween for contact with a thin mat suspended therebetween, means for applying a voltage to said one of said moveable electrode plates, means on said support means for feeding mat material from said forward portion for windup on a take-up roll mounted on said rearward portion and for movement between said pairs of electrode plates, and said other plate in each of said pair of plates having quick disconnect means to provide means for quickly replacing said one plates.

9. An apparatus for the testing of the electrical non-conductivity of a rubberized mat as set forth in claim 8 wherein said other plate in each pair of plates is of lesser width than said one plate in each pair of plates, and a vertically extending strip of magnetized electrically non-conductive material lies on each of said one plates in alignment with an edge of said other plate to prevent arcing from said one plate to an adjacent other plate in said pairs of plates.

* * * * *